United States Patent [19]

Benardelli

[11] 4,400,249

[45] Aug. 23, 1983

[54] PARTIAL SYNTHESIS PROCESS FOR PREPARING (+)-VINCAMINE AND RELATED INDOLIC ALKALOIDS

[75] Inventor: Giovanni Benardelli, Lugano, Switzerland

[73] Assignee: Linnea S.A., Lugano, Switzerland

[21] Appl. No.: 272,383

[22] Filed: Jun. 10, 1981

[30] Foreign Application Priority Data

Sep. 30, 1980 [CH] Switzerland ..................... 7290/80

[51] Int. Cl.³ ............................................. B01J 19/12
[52] U.S. Cl. .............................................. 204/158 R
[58] Field of Search ....................... 204/158 R, 158 N

[56] References Cited

U.S. PATENT DOCUMENTS 4,230,854 10/1980 Beacco et al. .................. 204/158 N Primary Examiner—Howard S. Williams
Attorney, Agent, or Firm—Irving M. Weiner; Pamela S. Burt; John L. Shortley

[57] ABSTRACT

A process of partial synthesis of vincamine and related indolic alkaloids for use as the active principal ingredient in drugs for treatment of diseases of the circulatory system and the central nervous system. The process includes the technique of activating oxygen in the elementary state in situ into an excited singlet state for chemical reaction by subjecting a reaction mixture to gaseous oxygen blowing under substantially ambient temperature and pressure conditions while effecting irradiation of the mixture by a light source. Operating conditions of the partial synthesis process are simplified, treatment times are reduced, and conversion yields are high.

17 Claims, No Drawings

PARTIAL SYNTHESIS PROCESS FOR PREPARING (+)-VINCAMINE AND RELATED INDOLIC ALKALOIDS

BACKGROUND OF THE INVENTION

1. Field of the Invention

This invention relates to a so-called partial synthesis process for preparing (+)-vincamine and related indolic alkaloids, which may be represented by the general formula (I):

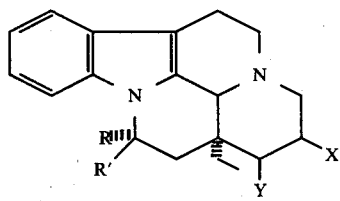

wherein:
(a) when X=Y=H, R'=—OH, R=—COOCH₃, formula (I) represents vincamine,
(b) when X=Y=H, R'=—COOCH₃, R=—OH, formula (I) represents 16-epivincamine,
(c) when X+Y=a double bond, R'=—OH, R=—COOCH₃, formula (I) represents Δ¹⁴-vincamine,
(d) when X+Y=a double bond, R'=—COOCH₃, R=—OH, formula (I) represents Δ¹⁴-16-epivincamine.

2. Description of Relevant Art

Vincamine is a member of a class of indolic alkaloids having interesting pharmacological properties, in particular of the hypotensive, sedative and cerebral metabolism activating kinds.

These characteristics render vincamine to be the active principal ingredient of effective drugs in the treatment of diseases of the circulatory system and of the central nervous system.

Methods for preparing vincamine and other indolic alkaloids on an industrial scale can be grouped into three distinct types of methods:
(a) extractive method;
(b) total synthesis; and
(c) partial synthesis.

Processes of direct extraction from vegetal species have limited applications due to the fact that, among plants, which are known as possible sources of vincamine, such a substance is contained therein in a very low amount (0.1-0.2%). This fact makes the extraction processes and more particularly the purification processes substantially complex and difficult, and is the cause of the high disproportion existing between the amount of starting vegetal product, solvents and reagents required, and the amount of substance obtained with an acceptable purity level.

The processes of total synthesis, or preparation from simple chemical compounds which are readily commercially available, present the advantage of requiring no vegetal products. However, due to the complexity of the chemical structure of vincamine, all the processes of this kind comprise a large number of steps, which together with other intrinsic problems (i.e., stereoselectivity of the reactions, separations of diastereoisomers and finally the obtaining of (+)-vincamine from racemic vincamine) cause significant decreases in the yield of final product. In processes of partial synthesis of compounds represented by formula (I), one particular process provides for use of structurally complex substances as starting materials, such as vincadifformine and tabersonine which are compounds included in the series of compounds represented by general formula (II):

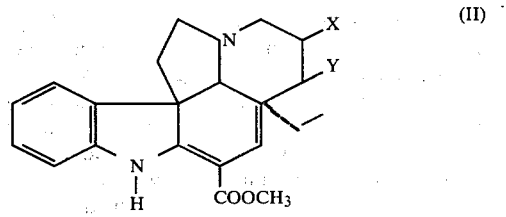

wherein:
(e) when X=Y=H, formula (II) represents vincadifformine, and
(f) when X+Y=a double bond, formula (II) represents tabersonine Compounds (II) are obtainable with a good yield from vegetal species which are widespread in nature. Vincadifformine can also be suitably prepared by catalytic hydrogenation of tabersonine [N. N. Janot, J. Le Men, Compt. Rend. Acad. Sci. 248,3005 (1959) et N. Plat, J. Le Men et N. N. Janot, Tetr. lett. 271 (1962)]. The substances (II) are then transformed into compounds (I) through a limited series of chemical steps.

Various processes of partial synthesis of vincamine or related alkaloids have been proposed, more particularly aiming at simplifying the operative steps and reducing duration thereof. An advance in this respect has been obtained with the reaction of direct oxidation of vincadifformine and/or tabersonine, in direct combination with specific compounds. French Pat. Nos. 75-24708 and 76-21432 can be cited in this connection. French Pat. No. 75-24708 describes a process for preparing vincamine and related alkaloids this process being based on the treatment of vincadifformine and/or tabersonine with oxygen over extended periods (5-10 days) in the presence of salts of copper, iron or cobalt, in an acid hydroalcoholic reaction medium. The main product and others are isolated by column chromatography of the crude reaction product. French Pat. No. 76-21432 describes a process according to which vincadifformine or tabersonine is first treated with sodium hydride in anhydrous tetrahydrofuran and hexamethylene phosphortriamide, in mixture with anhydrous dimethylformamide and toluene, in the presence of trimethyl phosphite. Thereafter, the solution is maintained under an oxygen atmosphere, then acidified and conventionally treated. The crude reaction product is finally subjected to column chromatography and thus vincamine is obtained with a yield of 28%.

The foregoing processes, while they may have adopted more acceptable techniques with respect to prior processes maintain, however, as in French Pat. No. 75-24708 operation durations which are still too long or, as in the case of French Pat. No. 76-21432, operating conditions which require difficult manipulation of reactants and restrictive and critical conditions of working temperature.

In other terms, vincadifformine and tabersonine, which are inert to the direct action of elementary oxygen, become reactive only in the presence of metal compounds (French Pat. No. 75-24708) or strong bases (French Pat. No. 76-21432) (which in an anhydrous environment transform vincadifformine and tabersonine into respective bidentated anions), because under these reactions a reaction between the thus activated substrates and elementary oxygen provides desired products in varying yields.

SUMMARY OF THE INVENTION

The object of the present invention is to provide a process of partial synthesis of vincamine and related indolic alkaloids having the general formula (I) from one of the compounds having the formula (II), which process does not require activation of the foregoing compounds, consequently develops under simple operating conditions within very short time periods and gives a very satisfying conversion yield.

More particularly, such a process provides the preparation of vincamine (I-a) as a main product and of 16-epivincamine (I-b) as secondary product from vincadifformine (II-e) and the preparation of $\Delta^{14}$-vincamine (I-c) as a main product and of $\Delta^{14}$-16-epivincamine (I-d) as a secondary product from tabersonine (II-f).

According to the present invention, physico-chemical techniques are taken into consideration, according to which oxygen in the elementary state is activable in situ into an excited singlet state for chemical reaction.

DETAILED DESCRIPTION OF PREFERRED EMBODIMENTS

According to prior art documents (SINGLET OXYGEN, B. Randy and J. Rabek, Ed. J. Wiley—Reaction with organic compounds and polymers, page 36), the process of photochemical activation can be represented as follows:

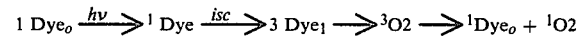

or

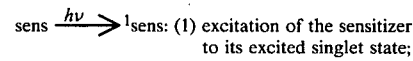 (1) excitation of the sensitizer to its excited singlet state;

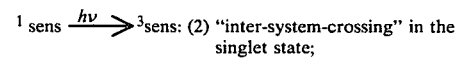 (2) "inter-system-crossing" in the singlet state;

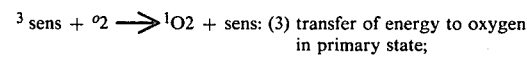 (3) transfer of energy to oxygen in primary state;

and

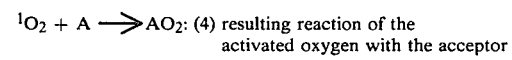 (4) resulting reaction of the activated oxygen with the acceptor

The process according to the invention comprises the following combination of steps:
a compound of general formula (II):

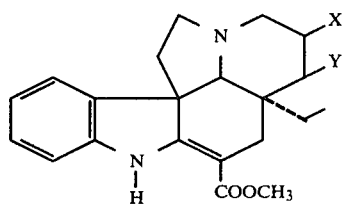

wherein:

(e) when $X=Y=H$, formula (II) represents vincadifformine, and (f) when $X+Y=$a double bond, formula (II) represents tabersonine, is used as the starting substrate,
the reaction medium comprising a low molecular weight alcohol, a trialkyl phosphite as a reducing agent and the photosensitizer is prepared,
the substrate is added to the reaction medium, the trialkyl phosphite being present in a stoichiometrical excess with respect to the substrate,
the thus formed reaction mixture is subjected to gaseous oxygen blowing under substantially ambient temperature and pressure conditions and at the same time the mixture is subjected to an irradiation from a light source in order to activate oxygen in situ, for a time not exceeding 150 minutes, thus obtaining oxidation of the substrate and a resulting reduction,
the treated reaction mixture is acidified, alkalized and extracted,
and finally the extraction residue is subjected to fractional crystallization and/or column chromatography in order to separate distinct products in the pure state, having the general formula (I).

Methanol may be used as a solvent, and triethyl phosphite in an excess of 1.1–1.5 equivalents with respect to the substrate may be used as a reducing agent. As photosensitizers, Rose Bengal (3′,6′-dichloro-2,4,5,7-tetraiodofluoresceine-disodium salt), eosine-yellowish (2′,4′,5′,7′-tetrabromo-fluoresceine-disodium salt), hematoporphyrin (7,12-bis(1-hydroxyethyl)-3,8,13,17-tetramethyl-21H,23H-porphine-2,18-dipropanoic acid) may be used, for example. If desired, the sensitizer which is present in the reaction medium preferably in an amount between 0.006°/$_{oo}$ and 0.1% (by weight/volume) with respect to the reaction medium, is stabilized in the same medium, for example, by addition of a base such as sodium hydroxide or sodium carbonate. The thus obtained reaction mixture is subjected to an oxygen blowing, preferably equal to 5–10 l/hour under substantially ambient temperature (20°–25°) and pressure conditions for a period of 30 to 90 minutes and at the same time it is exposed to the irradiation of an incandescent lamp.

If for treatment with oxygen, atmospheric air is used, the reaction mixture is subjected to an air blowing of 5–10 l/hour for 60–150 minutes under substantially ambient temperature and pressure conditions. The term "substantially ambient" as used herein in relation to temperature and pressure, refers to temperature and pressure which can deviate in slight excess from traditional values, namely beyond 15° C. and 1 atmosphere respectively. In the process according to the invention, oxygen in the primary state is activated into oxygen excited to the singlet state by action of an irradiation emitted by a light source in the presence of a photosensitizer.

Activated oxygen ($^1O_2$) generated from elementary oxygen reacts with tabersonine or vincadifformine so as to produce tabersonine hydroperoxide or vincadifformine hydroperoxide. These hydroperoxides, in the presence of reducing agents such as alkyl phosphites [see in general L. Fieser and M. Fieser in "Reagents for Org. Synt.; Vol. 1, page 1213 (1967), Ed. J. Wiley] and in an acid medium, are transformed into compounds (I). In particular, vincadifformine hydroperoxide is transformed into a mixture essentially comprised of vincamine and 16-epivincamine from which vincamine is obtained in pure state by fractional crystallization and/or column chromatography, while tabersonine hydroperoxide is analogously transformed into a mixture of $\Delta^{14}$-16-epivincamine and $\Delta^{14}$-vincamine from which the distinct compounds are isolated in the pure state by fractional crystallization and/or column chromatography. Several examples are given hereinafter.

EXAMPLE 1

2 gr of vincadifformine was dissolved in 140 ml of technical methyl alcohol containing 0.006°/$_{oo}$ (weight/volume) of Rose Bengal as photosensitizer. 5 ml of NaOH 2 N and 1.5 ml of triethyl phosphite were added and irradiation was effected with a tungsten lamp of 300 W for about 1 hour, maintaining a constant flow of oxygen and a temperature of 20°-25° C. in the solution. After the reaction was complete, the solution was concentrated under reduced pressure into a residue, and the latter was taken up with chloroform and filtered on neutral alumina. The solvent was dry evaporated, the residue was taken up with a mixture of MeOH/AcOH 1 M (1/1) while heating to 60° C. for 20-30 minutes. Then, the mixture was cooled, alkalized to pH 8.5-9 with concentrated ammonium hydroxide and extracted with chloroform. The organic extracts were combined, washed with water, dried on anhydrous sodium sulfate, filtered and concentrated into a residue. The residue was recrystallized from methyl alcohol and/or acetone.

About 1 gr of vincamine (yield of 50%) and about 0.4 gr of 16-epivincamine were obtained. The physico-chemical data of the products thus obtained were identical to those of corresponding reference compounds.

EXAMPLE 2

500 mgr of vincadifformine was dissolved in 75 ml of methyl alcohol containing 0.0066°/$_{oo}$ (weight/volume) of dihematoporphyrin as a sensitizer.

350 ml of triethyl phosphite and 0.25 ml of NaOH 2 N were added and irradiation was effected with a tungsten lamp, while a flow of oxygen (5-10 l/hour) was passed through the solution at 20° C. for about 90 minutes.

After the reaction was complete, the solution was diluted with 75 ml of water containing 10 ml of glacial acetic acid and 1 gr of trihydrate sodium acetate and boiled for 20 minutes. The solution was concentrated to half its volume, alkalized with NH$_4$OH and extracted with ACOEt. The organic phase was washed with water, dried on anhydrous Na$_2$SO$_4$, filtered and concentrated into a residue under reduced pressure. Recrystallization was then provided from methyl alcohol and/or acetone.

250 mgr of pure vincamine (yield of 47%) and 50 mgr of pure 16-epivincamine (yield of 9.5%) were obtained.

EXAMPLE 3

The same procedure as in Example 1 was employed, using air instead of oxygen. In this case, for completing the reaction, irradiation and air blowing were extended to 120-150 minutes. The yields of pure vincamine and pure 16-epivincamine were analogous to those of Example 1.

EXAMPLE 4

500 mgr of vincadifformine was dissolved in 75 ml of methanol containing 0.066°/$_{oo}$ of eosine as a sensitizer. 0.25 ml of NaOH 2 N, and 350 ml of (ETO)$_3$P were added and irradiation was provided with a tungsten lamp, maintaining a O$_2$ flow equal to 5-10 l/hour for 60 minutes at 20° C. in the solution. After the reaction was complete, the solution was diluted to 300 ml with H$_2$O containing 10 ml of CH$_3$COOH and 1 gr of CH$_3$COONa.3H$_2$O and refluxed for 20 minutes.

Then cooling and treating according to the operating procedures of Example 1 were provided.

230 mgr of vincamine (yield of 44%) and 70 mgr of epivincamine (yield of 13%) were obtained.

EXAMPLE 5

The same procedure as in Example 4, was employed using air instead of oxygen. For completing the reaction, irradiation and air blowing were extended to 120-150 minutes.

The conversion yields into pure vincamine and pure 16-epivincamine were analogous to those of Example 4.

EXAMPLE 6

1 gr of tabersonine was dissolved in 150 ml of methanol containing 0.0066% (weight/volume) of Rose Bengal as a photosensitizer. 2 ml of NaOH 2 N and 1.5 ml of triethyl phosphite were added and irradiation was provided with a tungsten lamp of 300 W for about 50 minutes, maintaining a constant flow of oxygen equal to 5-10 l/hour and a temperature of 20° C. in the solution. After the reaction was complete, the solution was concentrated to a residue under reduced pressure, taken up with chloroform and filtered on neutral alumina. The solvent was dry evaporated, the residue was taken up with 20 ml of glacial AcOH and 2 gr of AcONa.3H$_2$O, 150 ml of methanol was added and dilution was made to 300 ml with water, then refluxing was conducted for 15 minutes. The solution was cooled, alkalized at pH 8.5-9 with concentrated ammonium hydroxide and extracted with chloroform. The organic extracts were combined, washed with water, dried on sodium sulfate, filtered and concentrated into a residue. The residue was recrystallized from methanol. 600 mgr of $\Delta^{14}$-vincamine (yield of 57%) and 200 mgr of $\Delta^{14}$-16-epivincamine (yield of 19%) were obtained. The physico-chemical data of the obtained products were identical to those of corresponding reference compounds.

EXAMPLE 7

The same procedure as in Example 6 was employed, using air instead of oxygen. In such case, for completing the reaction, irradiation and air blowing were extended to 120-150 minutes. The yields of pure $\Delta^{14}$-vincamine and pure $\Delta^{14}$-16-epivincamine were analogous to those of Example 6.

From the preceding, the advantages of the process of the present invention are evident. Such process entails simple operating conditions, substantially ambient temperatures and a light source provided by an incandescent lamp. Moreover, with such a process, the chemical reactants and solvents which are employed are not aggressive, unstable or soil-forming. Finally, the combined times of treatment are within 2 to 3 hours, while the conversion yields are high.

We claim:

1. A process for preparing vincamine and other related indolic alkaloids represented by the general formula (I):

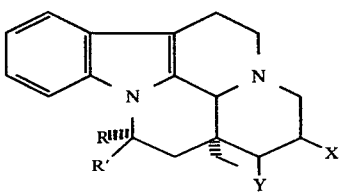

(I)

wherein:
(a) when X=Y=H, R'=—OH, R=—COOCH$_3$, formula (I) represents vincamine,
(b) when X=Y=H, R'=—COOCH$_3$, R=—OH, formula (I) represents 16-epivincamine,
(c) when X+Y=a double bond, R'=—OH, R=—COOCH$_3$, formula (I) represents $\Delta^{14}$-vincamine,
(d) when X+Y=a double bond, R'=—COOCH$_3$, R=—OH, formula (I) represents $\Delta^{14}$-16-epivincamine, comprising the steps of:
a compound of the general formula (II):

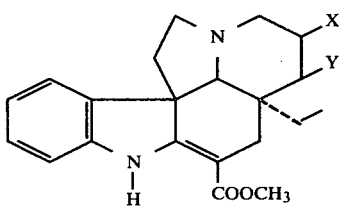

(II)

wherein:
(e) when X=Y=H, formula (II) represents vincadifformine, and
(f) when X+Y=a double bond, formula (II) represents tabersonine, is used as a starting substrate;
a reaction medium, comprising a low molecular weight alcohol, a trialkyl phosphite as a reducing agent, and a photosensitizer, is prepared;
said substrate is added to said reaction medium, said trialkyl phosphite being present in a stoichiometrical excess with respect to said substrate;
the thus formed reaction mixture is subjected to gaseous oxygen blowing under substantially ambient temperature and pressure conditions and at the same time said mixture is subjected to irradiation from a light source in order to activate oxygen in situ, for a time not exceeding 150 minutes, to obtain oxidation of said substrate and a resulting reduction;
the treated reaction mixture is acidified, alkalized and extracted;
and finally the extraction residue is subjected to fractional crystallization and/or column chromatography in order to separate distinct products represented by said general formula (I) in the pure state.

2. A process according to claim 1 for the preparation of said vincamine (I: X=Y=H, R=—COOCH$_3$, R'=—OH) as a principal product and of said 16-epivincamine (I: X=Y=H, R=—OH, R'=—COOCH$_3$) as a secondary product, wherein:
said vincadifformine (II: X=Y=H) is used as said starting substrate.

3. A process according to claim 1 for the preparation of said $\Delta^{14}$-vincamine (I: X+Y=a double bond, R=—COOCH$_3$, R'=—OH) and of said $\Delta^{14}$-16-epivincamine (I: X+Y=a double bond, R=—OH, R'=—COOCH$_3$), wherein:
said tabersonine (II: X+Y=a double bond) is used as said starting substrate.

4. A process according to claim 3, wherein:
said low molecular weight alcohol comprises methanol which is used as a solvent.

5. A process according to claim 4, wherein:
said trialkyl phosphite is used as a reducing agent in a 1.1 to 1.5 stoichiometrical excess with respect to said substrate.

6. A process according to claim 5, wherein:
said photosensitizer is present in said reaction medium in an amount between 0.006% and 0.1% (by weight/volume) with respect to said reaction medium.

7. A process according to claim 6, wherein:
said photosensitizer is a compound selected from the group consisting of:
the disodium salt of 2', 4', 5', 7'-tetrabromofluoresceine (eosine-yellowish);
the 7,12-bis(1-hydroxyethyl)-3,8,13,17-tetramethyl-21H,23H-porphin-2,18-dipropanoic acid (hematoporphyrin; and
the disodium salt of 3',6'-dichloro-2,4,5,7-tetraiodofluoresceine (Rose Bengal).

8. A process according to claim 7, wherein:
said photosensitizer is stabilized in said reaction medium by addition of a base, such as sodium hydroxide or sodium carbonate.

9. A process according to claim 8, wherein:
said reaction mixture is subjected to oxygen blowing equal to 5–10 liters/hour under substantially ambient conditions of temperature and pressure for a period of 30 to 90 minutes, while said mixture is subjected to light irradiation from an incandescent lamp.

10. A process according to claim 8, wherein:
said reaction mixture is subjected to oxygen blowing equal to 5–10 liters/hour for a period of 60–150 minutes under substantially ambient conditions of temperature and pressure, while said mixture is subjected to light irradiation from an incandescent lamp.

11. A process according to claim 1, wherein:
said low molecular alcohol comprises methanol which is used as a solvent.

12. A process according to claim 1, wherein:
said trialkyl phosphite is used as a reducing agent in a 1.1 to 1.5 stoichiometrical excess with respect to said substrate.

13. A process according to claim 1, wherein:
said photosensitizer is present in said reaction medium in an amount between 0.006% and 0.1% (by weight/volume) with respect to said reaction medium.

14. A process according to claim 13, wherein:
said photosensitizer is a compound selected from the group consisting of:
the disodium salt of 2',4',5',7'-tetrabromofluoresceine (eosine-yellowish);
the 7,12-bis(1-hydroxyethyl)-3,8,13,17-tetramethyl-21H,23H-porphin-2,18-dipropanoic acid (hematoporphyrin); and
the disodium salt of 3',6'-dichloro-2,4,5,7-tetraiodofluoresceine (Rose Bengal).

15. A process according to claim 1, wherein:

said photosensitizer is stabilized in said reaction medium by addition of a base, such as sodium hydroxide or sodium carbonate.

16. A process according to claim 1, wherein:
said reaction mixture is subjected to oxygen blowing equal to 5–10 liters/hour under substantially ambient conditions of temperature and pressure for a period of 30 to 90 minutes, while said mixture is subjected to light irradiation from an incandescent lamp.

17. A process according to claim 1, wherein:
said reaction mixture is subjected to oxygen blowing equal to 5–10 liters/hour for a period of 60–150 minutes under substantially ambient conditions of temperature and pressure, while said mixture is subjected to light irradiation from an incandescent lamp.

* * * * *